United States Patent [19]

de Nie-Sarink et al.

[11] Patent Number: 4,665,197

[45] Date of Patent: May 12, 1987

[54] PROCESS FOR PREPARING AZETIDINE DERIVATIVES AND INTERMEDIATES THEREOF

[75] Inventors: Margaretha J. de Nie-Sarink, Amsterdam, Netherlands; Ronald F. Mason, Ashford, England

[73] Assignee: Shell Oil Company, Houston, Tex.

[21] Appl. No.: 743,735

[22] Filed: Jun. 12, 1985

[30] Foreign Application Priority Data

Jun. 19, 1984 [GB] United Kingdom ................ 8415615

[51] Int. Cl.⁴ .......................................... C07D 205/04
[52] U.S. Cl. .................................... 548/953; 548/950
[58] Field of Search ................ 260/239 AR; 548/953

[56] References Cited

U.S. PATENT DOCUMENTS 4,569,795  2/1986  Scholes et al. ................ 260/239 A

FOREIGN PATENT DOCUMENTS 29265  5/1981  European Pat. Off. .
114079  7/1984  European Pat. Off. ..... 260/239 AR
1169027  10/1969  United Kingdom .

OTHER PUBLICATIONS

Nagasawa, et al., J. Med. Chem., vol. 16(5), (1973), pp. 583–585.
March, ed., Advanced Organic Chemistry, 2nd ed., (1977), McGraw-Hill, New York, pp. 569–572, 1107–1108.

Primary Examiner—Donald G. Daus
Assistant Examiner—William A. Teoli, Jr.

[57] ABSTRACT

The invention provides a process for preparing azetidine-3-carboxylic acid or salts thereof; useful as chemical hybridizing agents, which comprises treating a compound of the formula

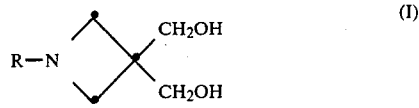

wherein R represents a hydrogen atom or a group of formula $R^1R^2CH$— wherein $R^1$ and $R^2$ are independently selected from hydrogen, alkyl or optionally substituted phenyl moieties, with nitric acid and subjecting the resulting initial product to acid conditions to produce an acid-addition salt of azetidine-3-carboxylic acid, and thereafter, if desired, converting the acid-addition salt to the free acid or another salt of the acid, 1-nitrosoazetidine-3,3-dicarboxylic acid, 1-nitrosoazetidine-3-carboxylic acid and salts thereof being intermediates in the process.

6 Claims, No Drawings

PROCESS FOR PREPARING AZETIDINE DERIVATIVES AND INTERMEDIATES THEREOF

BACKGROUND OF THE INVENTION

European Patent Application Publication No. 29265 discloses that 3-carboxyazetidine (azetidine-3-carboxylic acid) and related compounds are useful as plant hybridizing agents, based on their ability to produce male sterility in plants.

DESCRIPTION OF THE INVENTION

It has now been found that azetidine-3-carboxylic acid can be prepared by the nitric acid oxidation of a 3,3-bis(hydroxymethyl)azetidine, of the formula

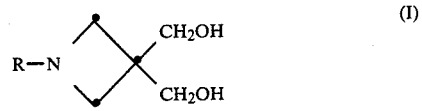

wherein R represents a hydrogen atom or a group of the formula $R^1R^2CH—$ wherein $R^1$ and $R^2$ are independently selected from hydrogen, alkyl (preferably $C_{1-6}$ alkyl) and optionally substituted phenyl moieties, by treating the compound of Formula I with nitric acid at a temperature of from about 35° C. to the reflux temperature of the mixture, then subjecting the resulting initial azetidine carboxylic acid product to acid conditions at a temperature above about 80° C. to produce an acid-addition salt of azetidine-3-carboxylic acid, and thereafter, if desired, converting the acid addition salt to the free acid or a different salt of the acid.

Optional substituents on a phenyl moiety include one or more substituents selected from the group consisting of $C_{1-4}$ alkyl, halogen, and nitro moieties.

Preferably at least one of $R^1$ and $R^2$ is hydrogen. Conveniently R represents a hydrogen atom or a group of the formula $R^1CH_2—$ wherein $R^1$ represents hydrogen, a $C_{1-3}$ alkyl group or a phenyl group.

The compound of formula I may conveniently be treated with nitric acid at a temperature in the range 35° C. to the reflux temperature of the reaction mixture, conveniently a temperature in the range 40° to 85° C. Temperatures in the range of 45° to 60° C. are very effective.

It is preferred that the concentration of nitric acid used in the treatment of the compound of formula I be at least 40% w/w. Conveniently the concentration of the nitric acid used is in the range 50 to 60% w/w.

Preferably the step of subjecting the initial product to acid conditions comprises treating the product with an aqueous acid selected from nitric, formic, acetic, hydrohalic (e.g. hydrochloric) and sulfuric acids. If nitric acid is used, its concentration is preferably 30% w/w or less.

The initial product is preferably subjected to acid treatment at temperatures above 80° C., more preferably above 90° C. Conveniently the initial product is subjected to acid conditions at the reflux temperature of the reaction mixture.

Those skilled in the art will appreciate that in acid conditions the azetidine-3-carboxylic acid product will generally exist as an acid-addition salt. If the acid is formic acid, it may be driven off with water when an aqueous solution is evaporated to dryness, to liberate the free acid. In other cases, acid-addition salts can readily be converted to the free acid, or to other acid-addition salts by conventional known methods.

The preparation of some compounds of formula I is described in UK Patent Specification No. 1,169,027 and other compounds of formula I may be prepared by analogous methods. Alternatively, compounds of formula I may be prepared by processes described hereinafter in detail, or by obvious modifications of such processes.

Intermediates which may be produced in the process of the invention include azetidine-3,3-dicarboxylic acid, 1-nitrosoazetidine-3,3-dicarboxylic acid and 1-nitrosoazetidine-3-carboxylic acid. Inter alia, azetidine-3,3-dicarboxylic acid is the subject of Applicants' co-pending patent application (K-0057 US), and the present invention further comprises azetidine-3-carboxylic acid derivatives of the formula

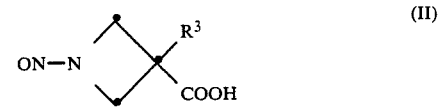

or salts thereof, wherein $R^3$ is hydrogen or —COOH.

The invention will be further understood from the following examples, of which Examples 1 to 7 illustrate the preparation of starting materials and Examples 8 to 19 illustrate processes in accordance with the invention.

EXAMPLE 1

Preparation of 3,3-bis(hydroxymethyl)-1-benzylazetidine (1)

(i) 60.0 g of 2,2-bis(bromomethyl)-1,3-propanediol was dissolved in 200 ml of ethanol and 10.1 g of 98% sodium hydroxide was added. The reaction mixture was stirred for 3 hours at reflux temperature, the solvent was evaporated under reduced pressure, the residue was taken up in diethyl ether and the solid material (sodium bromide) was removed by filtration. The resulting ethereal solution was evaporated to dryness. The residue was distilled under reduced pressure to yield 3-(bromomethyl)-3-(hydroxymethyl)oxetane (1A) as a clear, colorless oil, b.p.: 101°–110° C. at 1 Torr.

(ii) 18.1 g of 1A and 11.7 g of benzylamine were mixed with 5 ml of water and the resulting mixture was stirred at 100° C. After 4 hours the solution was allowed to cool to ambient temperature and 13.8 ml of 36% (w/w) hydrochloric acid was added. The resulting mixture was stirred at 60° C. After 2 hours the solution was again allowed to cool to room temperature and then washed with dichloromethane to remove by-products. The aqueous layer was made alkaline by the addition of a solution of 5.5 g of sodium hydroxide in 10 ml of water and stirred at 100° C. for 1 hour. After cooling to ambient temperature the pH of the mixture was raised by addition of another solution of 5.5 g of sodium hydroxide in 10 ml of water and washed with hexane to remove benzylamine. The water was evaporated under reduced pressure, and the solid residue was taken up in dichloromethane. Inorganic salts, which remained undissolved, were removed by filtration, and the dichloromethane was evaporated in vacuo, leaving 1, as a white crystalline solid.

EXAMPLE 2

Preparation of 3,3-bis(hydroxymethyl)azetidine (2)

7.5 g of 1A was taken up in 100 ml of 25% (w/w) aqueous ammonia and the mixture was stirred for 16 hours in an autoclave at 80° C. After evaporation of the aqueous ammonia, 10 ml of 48% (w/w) aqueous hydrobromic acid was added to the residue and the resulting solution was stirred at 60° C. After 2 hours the aqueous hydrobromic acid was evaporated, 75 ml of 25% (w/w) aqueous ammonia was added to the residue, and the resulting solution was stirred at 60° C. After 2 hours the aqueous ammonia was evaporated. The white, solid residue was freed from ammonium bromide by purification over "Dowex" 50W-X8 (H+) (registered Trademark) ion exchange resin, to yield crystalline 3,3-bis(hydroxymethyl)azetidine.

The above procedure may be effected using 2,2-bis(bromomethyl)-1,3-propanediol as starting material giving the same end product in similar yield. Alternatively, 3,3-bis(hydroxymethyl)azetidine may be prepared by debenzylation of 3,3-bis(hydroxymethyl)-1-benzylazetidine using hydrogen over palladium on carbon catalyst in methanol.

EXAMPLE 3

3,3-Bis(hydroxymethyl)-1-methylazetidine was prepared by a process similar to that of Example 2 using methylamine instead of ammonia.

EXAMPLE 4

3,3-Bis(hydroxymethyl)-1-ethylazetidine was prepared by a process similar to that of Example 2 using ethylamine instead of ammonia.

EXAMPLE 5

3,3-bis(hydroxymethyl)-1-isopropylazetidine was prepared by a process similar to that of Example 2 using isopropylamine instead of ammonia.

EXAMPLE 6

Preparation of 3,3-bis(hydroxymethyl)-1-benzylazetidine (1)

(i) A mixture of 10 g of 2,2-bis(bromomethyl)-1,3-propanediol, 5 ml of acetone and a catalytic quantity (0.1 g) of p-toluenesulfonic acid was heated under reflux in 150 ml of benzene until the theoretical amount of water (0.8 ml) had been collected in a Dean-Stark trap (2 hours). Evaporation of the solvent gave 5,5-bis(bromomethyl)-2,2-dimethyl-1,3-dioxane (6A), as a solid, m.p.: 56°-58° C. The purity according to gas-liquid chromatography and proton NMR was 99%.

(ii) A mixture of 28.5 g of 6A and 12.0 g of sodium carbonate in 50 ml of dimethyl sulfoxide (DMSO) was heated to 135° C. To the mixture was added dropwise with stirring a solution of 13.5 g of benzylamine in 50 ml of DMSO over a period of 5 to 6 hours. When the addition had been completed the reaction mixture was stirred for 7 hours at 135° C. After cooling, 10 ml of water was added and the whole was extracted with pentane. The pentane extract was washed with water, dried and evaporated. Distillation of the residue under reduced pressure gave 3,3-bis(hydroxymethyl)-1-benzylazetidine acetone acetal (6B) as a colorless oil b.p.: 135°-136° C. at 2 Torr.

(iii) 10 g of 6B was heated for 2 hours at 50° C. in 25 ml of 5% w/w sulfuric acid, then the resulting mixture was cooled to ambient temperature and made basic with 10% (w/w) sodium hydroxide solution. Extraction with ethyl acetate gave after drying and evaporating, an off-white solid. Recrystallization from toluene then gave 1, as white crystals, m.p.: 86°-87° C.

EXAMPLE 7

Preparation of 3,3-bis(hydroxymethyl)-1-benzylazetidine (1)

A mixture of 30.2 g of 5,5-bis(bromomethyl)-2,2-dimethyl-1,3-dioxane (0.1 mol), 24.0 g of sodium bicarbonate and 50 ml of dimethyl sulfoxide was heated to 135° C. A solution of 10.7 g of benzylamine in 50 ml of DMSO was then added dropwise with stirring over 1.5 hours. After addition was complete, the mixture was stirred for 2.5 hours at 135° C. After cooling, 100 ml of DMSO and 20 ml of water were added and the solution was extracted with pentane. The extract was washed with water and then shaken with 5% (w/w) sulfuric acid in order to extract the basic 3,3-bis(hydroxymethyl)-1-benzylazetidine acetone acetal.

The acidic aqueous layer was heated for 1 hour at 50° C. and then evaporated nearly to dryness. The residue was made basic with 10% (w/w) sodium hydroxide and the water was evaporated under reduced pressure. Ethanol was added and the insolubles were filtered off. Evaporation of the ethanol from the filtrate left a white solid which on recrystallization from toluene gave 1, as white crystals m.p.: 86.2°-86.8° C.

EXAMPLE 8

Preparation of azetidine-3-carboxylic acid (i) 10 g of 1 was dissolved in 100 ml of 55%w/w aqueous nitric acid and the resulting mixture was stirred for 18 hours at 50° C. Benzoic acid precipitated out as a white solid and was filtered off. The filtrate was evaporated to dryness, 50 ml of water was added to the residue and the resulting solution was evaporated to dryness. The latter step was repeated three times. The residue was then dissolved in 50 ml of water and the solution was extracted with diethyl ether to extract any remaining benzoic acid. Evaporation of the water phase left 1-nitrosoazetidine-3,3-dicarboxylic acid (8A).

(ii) To 7.3 g of 8A was added 10 ml of water and 40 ml of formic acid. The resulting mixture was heated for 5 hours at 110° C. Nitrous fumes evolved. The mixture was then evaporated to dryness, yielding a brown oil which was shown by high pressure liquid chromatography against standard material to contain 43.5%w of azetidine-3-carboxylic acid.

EXAMPLES 9 AND 10

The products of Example 3, 3,3-bis(hydroxymethyl)-1-methylazetidine, and of Example 4, 3,3-bis(hydroxymethyl)-1-ethylazetidine, were oxidized under the conditions of Example 8(i), and in each case the product was 1-nitrosoazetidine-3,3-dicarboxylic acid.

EXAMPLES 11-13

Oxidation of 3,3-bis(hydroxymethyl)-1-benzylazetidine 3,3-bis(hydroxymethyl)-1-benzylazetidine was oxidized with nitric acid by similar general procedures to that of Example 8(i) but with variations in concentrations and conditions. Results are given in Table 1 following.

TABLE 1

| Example | Scale (g) | Nitric Acid Conc. (w/w) | Temp. (°C.) | Conc. of Azetidine Starting Material (g/ml) | Reaction Time (hours) | Product |
|---|---|---|---|---|---|---|
| 11 | 1 | 65 | 50 | 1/5 | 18 | 1-nitroso-azetidine-3,3-dicarboxylic acid |
| 12 | 5 | 55 | 50 | 1/10 | 16.5 | 1-nitroso-azetidine-3,3-dicarboxylic acid |
| 13 | 2.5 | 55 | 50 | 1/20 | 18 | 1-nitroso-azetidine-3,3-dicarboxylic acid & azetidine-3,3-dicarboxylic acid |

EXAMPLES 14–16

Oxidation of 3,3-bis(hydroxymethyl)azetidine 3,3-bis(hydroxymethyl)azetidine was oxidized with nitric acid by procedures comparable with those of Example 8(i). Experimental conditions and results are given in Table 2 following.

TABLE 2

| Example | Nitric Acid Conc. (w/w) | Temp. (°C.) | Conc. of Azetidine Starting Material (g/ml) | Reaction Time (hours) | Product |
|---|---|---|---|---|---|
| 14 | 55 | 50 | 1/20 | 16.5 | 1-nitroso-azetidine-3,3-dicarboxylic acid |
| 15 | 55 | 50 | 1/15 | 4 | 1-nitroso-azetidine-3,3-dicarboxylic acid |
| 16 | 55 | 50 | 1/20 | 18 | 1-nitroso-azetidine-3,3-dicarboxylic acid & azetidine-3,3-dicarboxylic acid |

EXAMPLES 17–19

Conversion of 1-nitrosoazetidine-3,3-dicarboxylic acid

1-Nitrosoazetidine-3,3-dicarboxylic acid was subjected to acid treatment following procedures comparable with that of Example 8(ii). Experimental conditions and results are given in Table 3 following. Comparative Example A demonstrates that acid conditions are necessary for full conversion, but demonstrates that 1-nitrosoazetidine-3-carboxylic acid is an intermediate in conversion of 1-nitrosoazetidine-3,3-dicarboxylic acid to azetidine-3-carboxylic acid.

TABLE 3

| Example | Acid Concentration (w/w) | Temp. (°C.) | Reaction Time (hours) | Product |
|---|---|---|---|---|
| 17 | hydrochloric, 9% w/w | reflux | 16.5 | azetidine-3-carboxylic acid hydrochloride (pale yellow solid) |
| 18 | hydrochloric, 3.6% w/w | reflux | 16.5 | azetidine-3-carboxylic acid hydrochloride (pale yellow solid) |
| 19 | formic acid 80% v/v | reflux | 16.5 | azetidine-3-carboxylic acid (dark brown oil) |
| Comparative (A) | water | reflux | 16.5 | resulting solution contained mixture of 1-nitrosoazetidine-3,3-dicarboxylic acid, 1-nitrosoazetidine-3-carboxylic acid and azetidine-3-carboxylic acid in molar ratio 1:4:2 |

We claim:

1. A process for preparing azetidine-3-carboxylic acid or a salt thereof, that comprises treating a compound of the formula

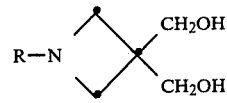

wherein R represents a hydrogen atom or a group of the formula $R^1R^2CH-$ wherein $R^1$ and $R^2$ are independently selected from hydrogen, alkyl and phenyl, with nitric acid at a temperature of from about 35° C. to the reflux temperature of the mixture, then subjecting the resulting initial azetidine carboxylic acid product to acid conditions at a temperature above about 80° C. to produce an acid-addition salt of azetidine-3-carboxylic acid, and thereafter, if desired, converting the acid-addition salt to the free acid or a different salt of the acid.

2. A process according to claim 1 wherein R in formula I represents a hydrogen atom or a group of formula $R^1CH_2-$ wherein $R^1$ represents hydrogen, a $C_{1-3}$ alkyl group or a phenyl group.

3. A process according to claim 1 wherein the concentration of the nitric acid used is in the range 50 to 65% w/w.

4. A process according to claim 1 wherein subjecting the initial product to acid conditions comprises treating the product with an aqueous acid selected from nitric, formic, hydrochloric and sulphuric acids.

5. A process according to claim 4 wherein the initial product is subjected to acid conditions at the reflux temperature of the reaction mixture.

6. A compound of the formula

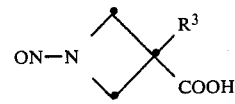

or a salt thereof wherein $R^3$ is hydrogen or —COOH.